(12) United States Patent
Parker et al.

(10) Patent No.: US 6,263,880 B1
(45) Date of Patent: Jul. 24, 2001

(54) METHOD OF ENHANCING BLOOD FLOW IN TISSUE

(75) Inventors: Theodore L. Parker, Danville; Danforth Joslyn, Santa Rosa; Serjan D. Nikolic, San Francisco, all of CA (US)

(73) Assignee: Neovasys, Inc., Hayward, CA (US)

( * ) Notice: Subject to any disclaimer, the term of this patent is extended or adjusted under 35 U.S.C. 154(b) by 0 days.

(21) Appl. No.: 09/337,622

(22) Filed: Jun. 21, 1999

Related U.S. Application Data

(60) Provisional application No. 60/090,279, filed on Jun. 22, 1998, and provisional application No. 60/090,400, filed on Jun. 22, 1998.

(51) Int. Cl.$^7$ .............................. A61F 2/02; A61B 17/00
(52) U.S. Cl. ...................... 128/898; 623/1.38; 623/1.42; 424/426
(58) Field of Search ........................ 128/898; 623/1.38, 623/1.42; 424/426

(56) References Cited

U.S. PATENT DOCUMENTS

| | | |
|---|---|---|
| 4,658,817 | 4/1987 | Hardy . |
| 5,021,241 | 6/1991 | Yamahira et al. . |
| 5,110,595 | 5/1992 | Wang . |
| 5,125,926 | 6/1992 | Rudko et al. . |
| 5,244,460 | 9/1993 | Unger et al. . |
| 5,326,568 | 7/1994 | Giampapa . |
| 5,429,144 | 7/1995 | Wilk . |
| 5,429,634 | 7/1995 | Narciso, Jr. . |
| 5,466,233 | 11/1995 | Weiner et al. . |
| 5,480,975 | 1/1996 | Goldberg et al. . |
| 5,484,403 | 1/1996 | Yoakum et al. . |
| 5,494,677 | 2/1996 | Giampapa . |
| 5,554,152 | 9/1996 | Aita et al. . |
| 5,580,569 | 12/1996 | Giampapa . |

(List continued on next page.)

FOREIGN PATENT DOCUMENTS 97 16176  5/1997  (WO) .

OTHER PUBLICATIONS

Sen et al., "Transmyocardial Acupuncture", Journal of Thoracic and Cardiovascular Surgery, vol. 50, No. 2, p. 181–189, Aug. 1965.

Whittaker et al., "Transmural Channels Can Protect Ischemic Tissue", Circulation, vol. 93, No. 1, p. 143–152, Jan. 1, 1996.

Hardy et al., "A Histologic Study of Laser–Induced Transmyocardial Channels", Lasers in Surgery and Medicine 6, p. 563–573, 1987.

Mack et al., "Channel Patency and Neovascularization After Transmyocardial Revascularization Using an Excimer Laser", Circulation, vol. 96, No. 9, II 65–69, 1997.

Kornowski et al., "Current Perspectives on Direct Myocardial Revascularization", The American Journal of Cardiology®, vol. 81 (7A), p. 44E–48E, Apr. 9, 1998.

Hoeckel et al, "Therapeutic Angiogenesis", Arch. Surg., vo. 128, pp. 423–429, Apr. 1993.*

Primary Examiner—Corrine McDermott
Assistant Examiner—Choon P. Koh
(74) Attorney, Agent, or Firm—Flehr Hohbach Test Albritton & Herbert LLP

(57) ABSTRACT

Method of enhancing blood flow in tissue wherein an implant is non-ablatively introduced into the tissue in order to stimulate production of angiogenic agents by the tissue, the agents produced by the tissue are absorbed into the implant, where they are stored, and the stored agents are released back into the tissue when the production of agents by the tissue subsides. The implant is fabricated of a bioresorbable material and is resorbed into the tissue after the agents are released. In some embodiments, an exogenous angiogenic agent in included in the implant and released into the tissue along with the agents which are produced by the tissue and absorbed by the implant.

26 Claims, 6 Drawing Sheets

U.S. PATENT DOCUMENTS

| | | |
|---|---|---|
| 5,591,161 | 1/1997 | Negus et al. . |
| 5,617,258 | 4/1997 | Negus et al. . |
| 5,652,225 | 7/1997 | Isner . |
| 5,672,170 | 9/1997 | Cho et al. . |
| 5,683,366 | 11/1997 | Eggers et al. . |
| 5,700,259 | 12/1997 | Negus et al. . |
| 5,713,894 | 2/1998 | Murphy-Chutorian et al. . |
| 5,723,147 | 3/1998 | Kim et al. . |
| 5,725,567 | 3/1998 | Wolff et al. . |
| 5,728,091 | 3/1998 | Payne et al. . |
| 5,738,680 | 4/1998 | Mueller et al. . |
| 5,810,836 | 9/1998 | Hussein et al. . |
| 5,840,059 | 11/1998 | March et al. . |
| 5,878,751 | 3/1999 | Hussein et al. . |
| 5,894,070 | 4/1999 | Hansson et al. . |
| 5,902,799 | 5/1999 | Herrmann et al. . |
| 5,971,993 | 10/1999 | Hussein et al. . |
| 5,980,548 | 11/1999 | Evans et al. . |
| 5,984,956 | 11/1999 | Tweden et al. . |

\* cited by examiner

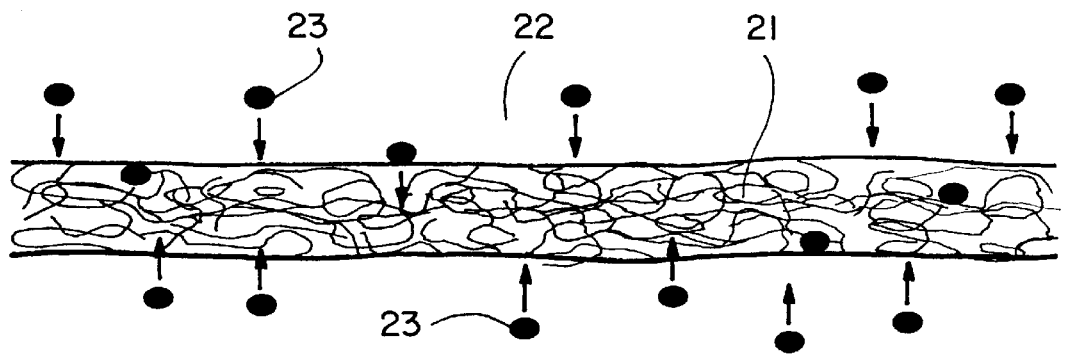
FIG_1A
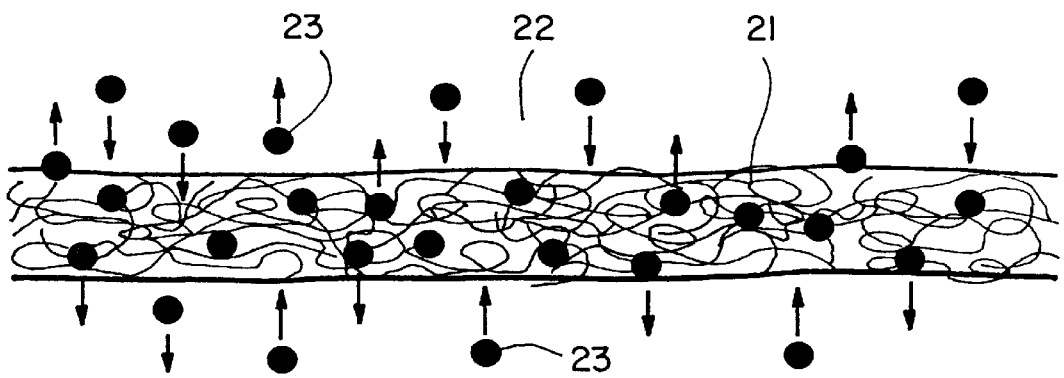
FIG_1B
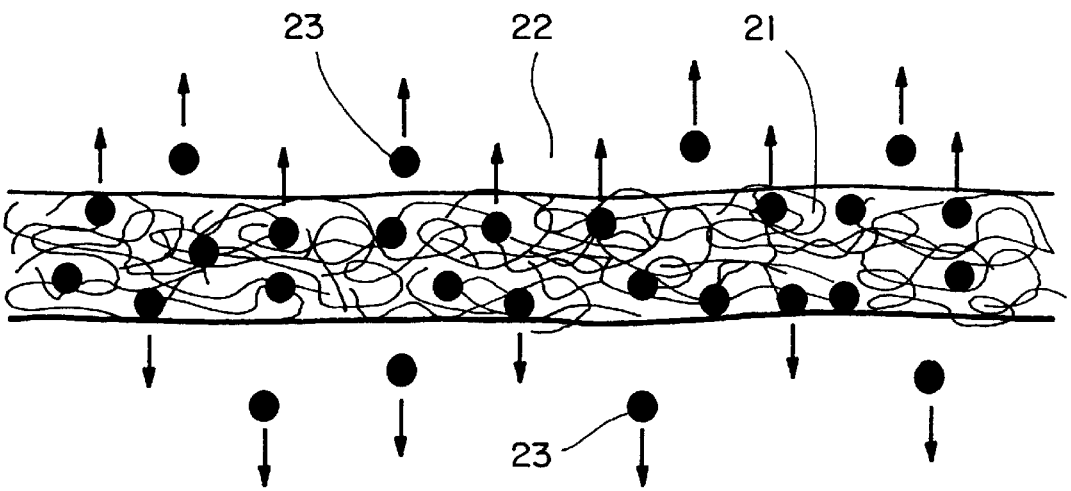
FIG_1C

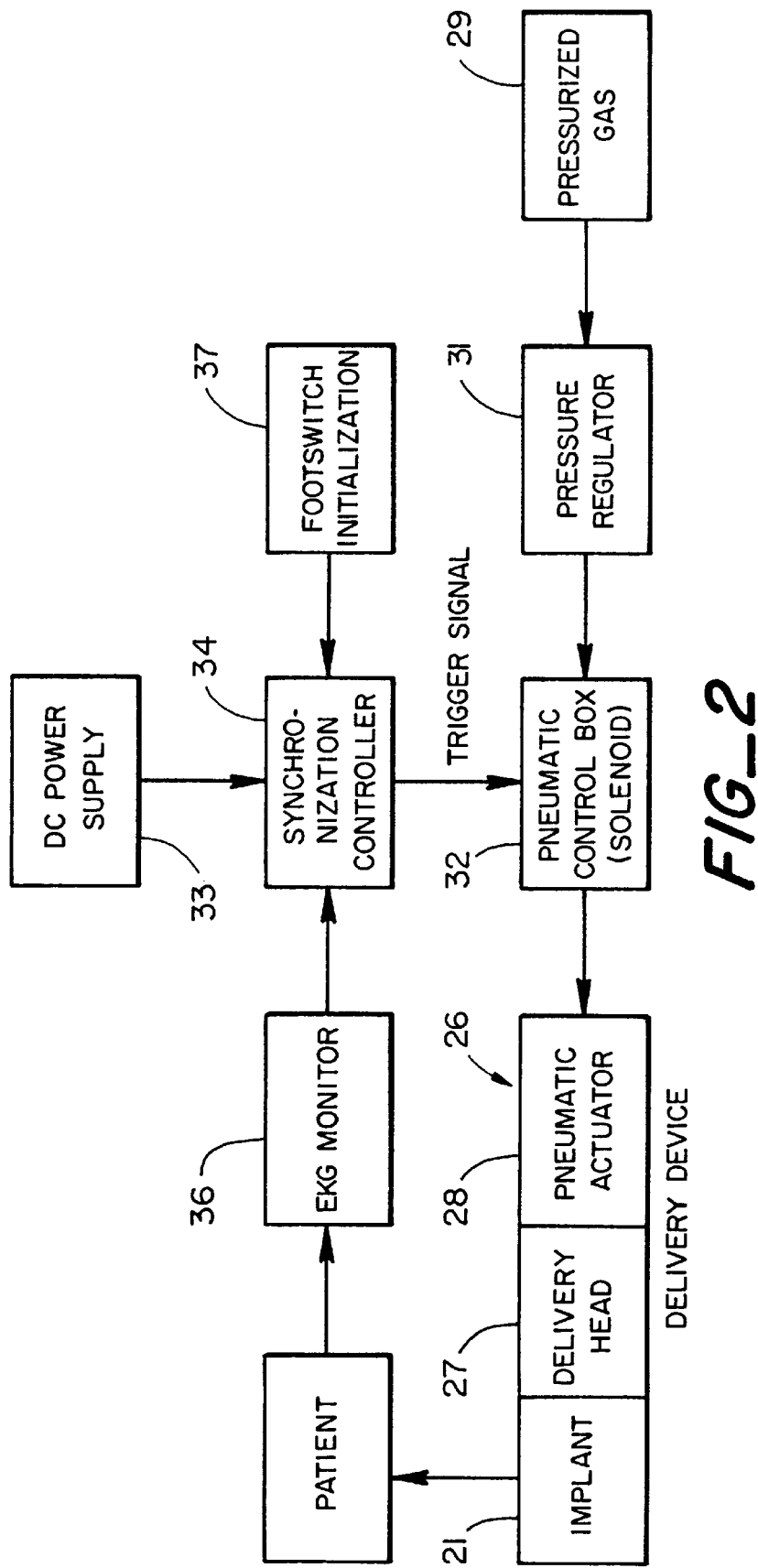
FIG_2

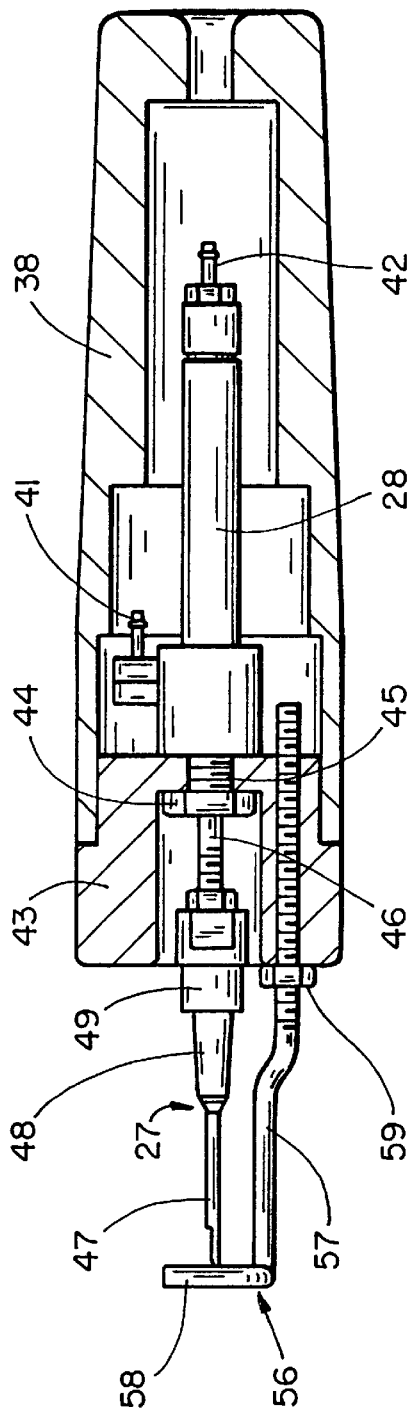
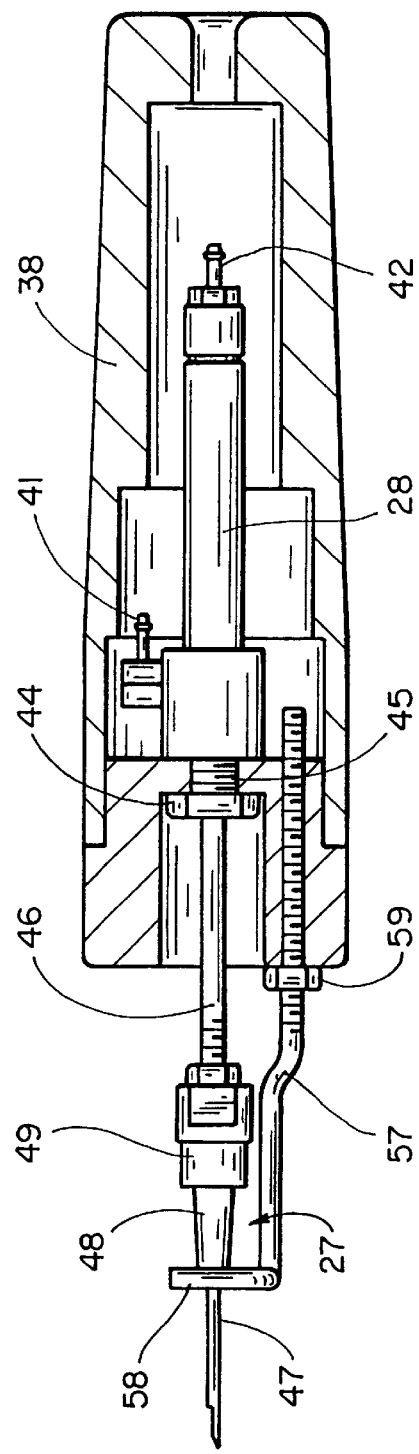

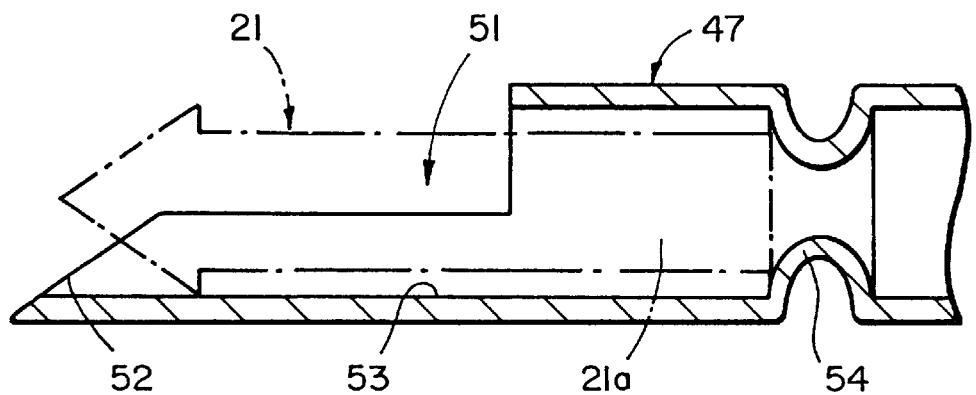
FIG_4
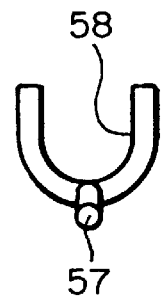
FIG_5
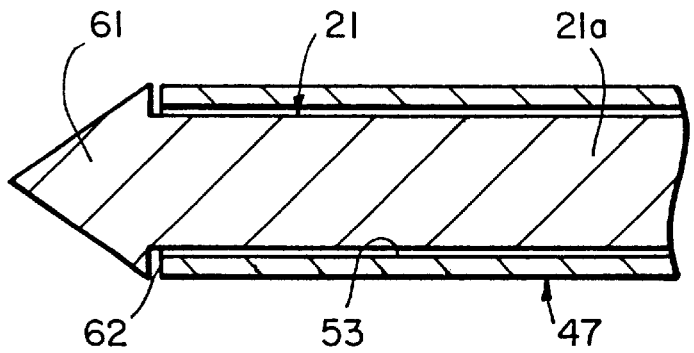
FIG_7

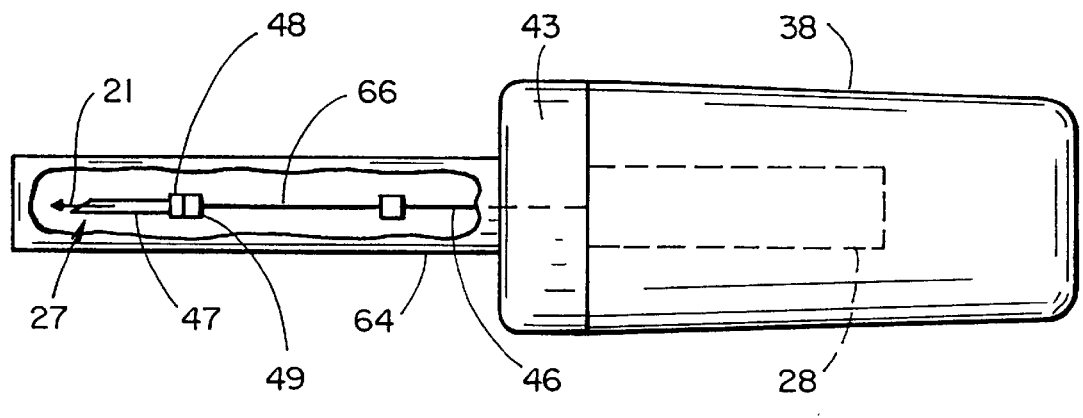
FIG_8
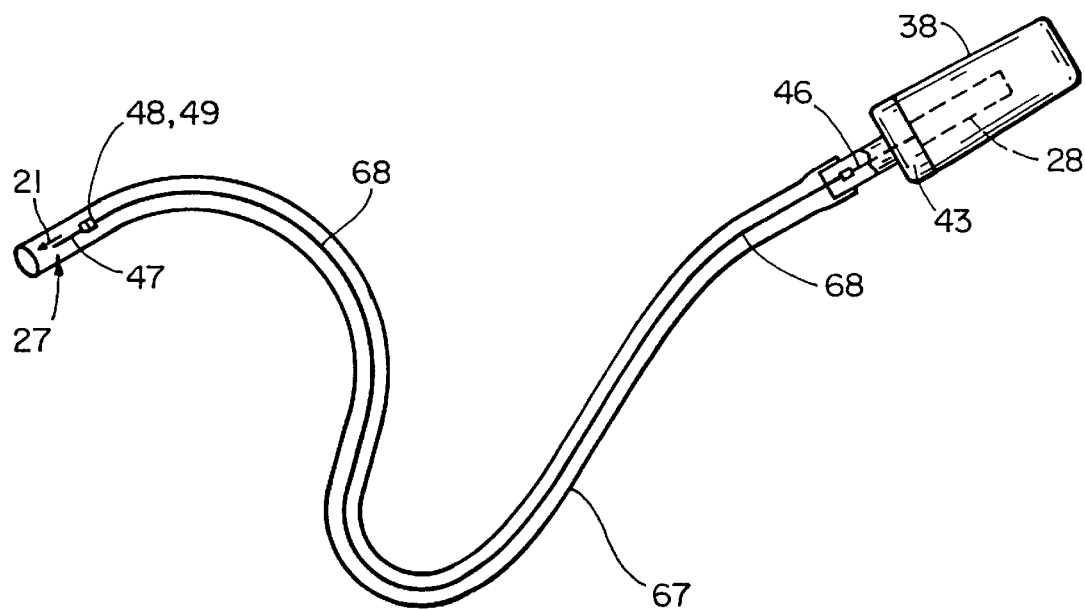
FIG_9

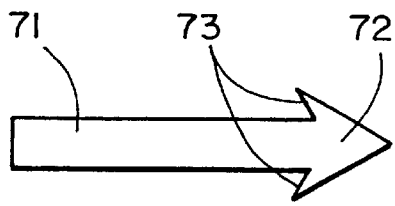
FIG_10
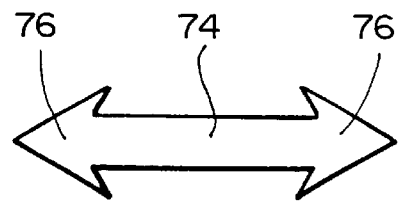
FIG_11
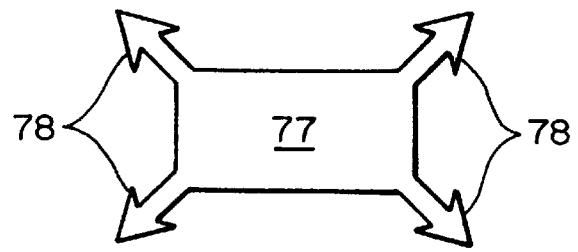
FIG_12
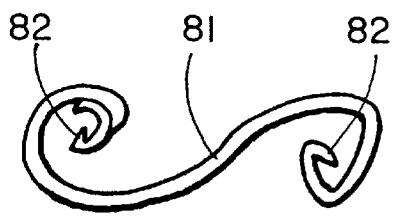
FIG_13
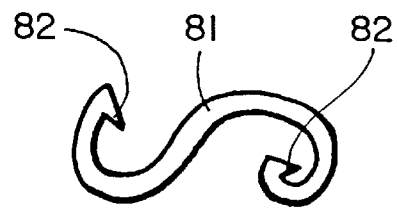
FIG_14
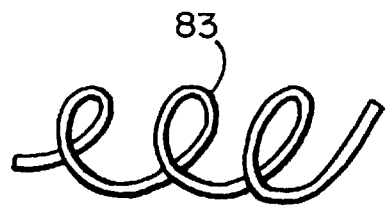
FIG_15

METHOD OF ENHANCING BLOOD FLOW IN TISSUE

This application is based upon Provisional Applications Nos. 60/090,279 and 60/090,400, filed Jun. 22, 1998.

This invention pertains generally to the treatment of living tissue and, more particularly, to a method of enhancing blood flow in tissue as, for example, in the treatment of ischemic heart disease.

Coronary by-pass surgery, balloon angioplasty, and stenting are now well-developed procedures for correcting reduced blood supply due to arterial blockage. Such procedures target large vessels and are not as effective in treating ischemic diseases where the pathology is centered in the small vessels, or where procedures such as coronary artery bypass grafting (CABG) or percutaneous transluminal coronary angioplasty (PTCA) are not medically indicated. New technologies are emerging for enhancing blood flow in the peripheral vascular system at the level of capillaries and arterioles. One of the most promising of these technologies is interventional angiogenesis in which the patient's own body is stimulated to grow new capillary beds or vessels and thereby improve the blood supply to the ischemic region. Interventional angiogenesis is a treatment for addressing small vascular disease, and can be used in conjunction with large vessel procedures such as CABG and PTCA.

Two basic interventional angiogenesis technologies which have been developed in recent years are transmyocardial revascularization (TMR) and angiogenic agent therapy. TMR involves the creation of channels in the myocardium to promote the release of the body's own angiogenic agents, and angiogenic agent therapy involves the injection of growth factors or growth vectors into the myocardium or vasculature.

TMR is used primarily in the treatment of patients with ischemic heart disease. In TMR, a number of small channels are created in the ischemic area of the myocardium to elicit a therapeutic response by stimulating angiogenic capillary formation, and thereby increase blood flow to the ischemic region. In clinical trials, TMR has shown new vessel growth in an ischemic region within a few weeks of treatment. As a result, many patients have experiences an immediate and dramatic reduction in angina symptoms and an improvement in cardiac function over time.

Laser TMR systems using $CO_2$ and YAG lasers, which recently received FDA approval for the treatment of Class IV angina, have demonstrated dramatic relief of Class III and Class IV angina along with new capillary growth. However, current laser-based systems have significant clinical and cost disadvantages which may prevent them from enjoying long-term market acceptance. Since the channels are created by ablation of the tissue, laser cutting can result in significant ancillary tissue damage to the myocardium. In addition, and possibly even more significant, laser treatment is not readily used in conjunction with new drug treatments which are currently under development and are expected to be available in a few years. Laser systems are also relatively expensive, and require special facilities and safety precautions.

There have also been some efforts to create revascularization channels in the myocardium by other means such as RF ablation and by the use of mechanical cutters. However, each of these techniques has its own limitations and disadvantages.

The direct application of growth factors into the myocardium is currently undergoing intensive early clinical investigation. Growth factors have been delivered (a) directly into the myocardium during coronary by-pass surgery or through a mini-thoracotomy, (b) intra-coronarally using a catheter, (c) intravenously via infusion, and (d) in laser TMR channels via syringe. Various growth factors have been used, including FGF-1 from strains of *E. Coli* (Cardio Vascular Genetic Engineering, Inc.), naked plasmid DNA encoding VEGF-165 (Human Genome Sciences, Inc.), adenovirus VEGF-121 (Gen Vec, Inc.), recombinant human VEGF-165 (Genentech, Inc.), human adenovirus-5 expressing human FGF-4 (Collateral Therapeutics, Inc.), bFGF incorporated into heparin-alginate microspheres, and hypoxia-inducible factor (HIF-1) (Genzyme).

Although the angiogenesis due to the application of growth factors can be demonstrated by imaging techniques, it is still uncertain whether any significant improvement in myocardial function will result. The process of angiogenesis is such a complex series of events that a one-time application of growth factor is not likely to yield optimal angiogenesis. There are also concerns that the direct application of growth factor may have negative side effects such as accelerating atherosclerosis, facilitating latent malignancy, hypotensive effects and others.

A variety of implantable drug delivery devices have heretofore been provided for use in controlled and sustained delivery of a medication in vivo to humans as well as to animals. Such implants have often been made from permeable, biodegradable and/or bioerodable materials, such as synthetic polymers. They are generally macroscopic in size and scale and are typically on the order of 3–10 mm in diameter and about 1–3 cm in length. They are typically designed to be sleek to allow ready insertion through an incision in the skin, and they have a tendency to migrate due to normal muscle contraction.

It is in general an object of the invention to provide a new and improved method of enhancing blood flow in tissue.

Another object of the invention is to provide a method of the above character which overcomes the limitations and disadvantages of the prior art.

These and other objects are achieved in accordance with the invention by non-ablatively introducing an implant into the tissue to be treated in order to stimulate production of angiogenic agents by the tissue, absorbing the agents produced by the tissue into the implant, storing the absorbed agents in the implant, and releasing the stored agents back into the tissue when the production of agents by the tissue subsides. The implant is fabricated of a bioresorbable material and is resorbed into the tissue after the agents are released. In some embodiments, an exogenous angiogenic agent is included in the implant and released into the tissue along with the agents which are produced by the tissue and absorbed by the implant.

FIGS. 1A–1C are schematic views illustrating the production, storage and release of angiogenic agents when a bioresorbable implant is non-ablatively introduced into tissue in accordance with the invention.

FIG. 2 is a simplified block diagram of one embodiment of a system for inserting implants into the heart tissue in accordance with the invention.

FIG. 3 is a cross-sectional view of one embodiment of an instrument for delivering an implant to tissue to be treated in accordance with the invention.

FIG. 4 is an enlarged, fragmentary sectional view of the delivery head in the embodiment of FIG. 3.

FIG. 5 is an end elevational view of the depth gauge in the embodiment of FIG. 3.

FIG. 6 is a view similar to FIG. 3, showing the delivery head in an advanced or extended position.

FIG. 7 is an enlarged, fragmentary cross sectional view of another embodiment of an implant and delivery head for use in the invention.

FIG. 8 is a side elevational view, partly broken away, of another embodiment of an instrument for inserting implants in tissue in accordance with the invention.

FIG. 9 is an isometric view, partly broken away, of another embodiment of an instrument for inserting implants in tissue in accordance with the invention.

FIGS. 10–15 are side elevational views of implants for insertion in tissue in accordance with the invention.

As illustrated in FIGS. 1A–1C, a bioresorbable implant 21 is non-ablatively introduced into the myocardium or tissue 22 to be treated. Although a preferred application of the invention is in the treatment of ischemic heart disease, it can also be used to enhance the function of hypoxic or ischemic tissue, or to increase the vascularity or blood flow of any other tissue.

Examples of hypoxic tissue with which the invention can be utilized include, but are not limited to, cardiac tissue, myocardial tissue, diabetic ulcers, surgical wounds, neuronal tissue, diffuse ischemic tissue, tissue damaged as a result of peripheral vascular disease, angina, atherosclerosis, ischemic renal, hepatic or cerebral tissue, and tissue generally suffering from poor circulation. The invention may be used for treatment of limb ischemia, ischemic cardiomyopathy, myocardial ischemia, bone fractures, frostbite, gangrene or portal hypertension.

The invention can be used as the primary method of treatment of small vessel heart diseases such as angina pectoris, and it can be used as an adjunct treatment to coronary artery by-pass graft (CABG) procedures, percutaneous transluminal coronary angioplasty (PTCA) procedures, and cardiac valve repair and/or replacement procedures.

Insertion of the implant elicits and stimulates the production of angiogenic agents 23 which promote new capillary growth or revascularization of the tissue. These agents are principally protein growth factors such as VEGF, aFGF, bFGF and PDGF growth factors, and angiopoietin. As discussed more fully hereinafter, the implant is fabricated of a material which enters the tissue in a relatively stiff state, then softens to form a compliant hydrodynamic polymer gel that can absorb the agents produced by the tissue.

Initially, as illustrated in FIG. 1A, the concentration of angiogenic agents 23 in the tissue surrounding the implant is high, and there is a net inflow of such agents into the implant. Because the agents absorbed by the implant are removed from the extracellular fluid, they cannot participate in feedback mechanisms, and the amount of agent produced by the cells is increased.

Thereafter, as illustrated in FIG. 1B, the implant becomes saturated with the angiogenic agents produced by the tissue and, in effect, becomes an in situ reservoir in which an equilibrium is reached between the absorption of agents by the implant and the release of agents back into the tissue.

When, as illustrated in FIG. 1C, the production of agents by the tissue falls off or subsides and the concentration of the agents in the tissue decreases, the agents stored in the implant continue to be released back into the tissue, thereby prolonging and enhancing the angiogenic response and revascularization of the tissue. The implant thus serves as a controlled local drug delivery system for an angiogenic agent.

The implant is fabricated of a biodegradable and/or bioresorbable material, and is resorbed into the tissue. The resorption process begins while the angiogenic agents are being absorbed and released, and continues until the resorption is complete. Typically, the implant is totally dissolved within about two weeks after introduction into the tissue.

Suitable bioresorbable polymers include poly hydroxy esters, poly dioxanones, poly vinyl pyrrolidone, poly ethylene oxide, poly ethylene oxide-poly propylene oxide copolymers, poly ortho esters, poly spiro esters, poly anhydrides, poly vinyl alcohol, poly acrylates, cellulose ethers, cellulose esters, proteins, poly saccharides, poly saccharide derivatives, and combinations thereof. Suitable proteins include gelatin, collagen, albumin, laminin, fibronectin, and combinations thereof.

The poly hydroxy esters can be selected from the group consisting of poly lactide, poly glycolide, poly L-lactide, poly lactide-glycolide copolymer, L-lactide-glycolide copolymer, poly caprolactone, glycolide caprolactone copolymer, glycolide-trimethylene carbonate copolymer, lactide-ethylene oxide copolymer, and combinations thereof.

The poly acrylates are selected from the group consisting of hydroxyethyl methacrylate, hydroxyethyl methacrylate-comethyl methacrylate, poly acrylic acid, poly methacrylates, poly lactide poly acrylate copolymers, poly glycolide poly acrylate copolymers, and combinations thereof.

Suitable poly saccharide derivatives include sulfated galactans, aminoglycans, proteoglycans, glycosaminoglycans, and combinations thereof. Suitable sulfated galactans, aminoglycans, proteoglycans and glycosaminoglycans include amino dextran, chitin, chitosan, carrageenan, alginin, xanthan gum, heparin, heparan sulfate, hirudin, chondroitin sulfate, dermatan sulfate, hyaluronan, and combinations thereof.

If desired, the implant material can be compounded with a biocompatible agent to increase the rate of bioresorption or biodegradation. Suitable compounding agents include an ester, ether or hydrocarbon, such as triethyl citrate, acetyl tributyl citrate, acetyl trihexyl citrate, ethyl stearate, ethyl laurate, ethyl palmitate or fatty acid esters or glycerides; poly (ethylene oxide), poly (ethylene glycol); mineral oil, petroleum jelly; a polysaccharide, lecithin, choline, or phospatidyl choline.

The agents which are produced by the tissue are released sequentially in a cascade fashion, and the implant is fabricated of or contains one or more materials which can provide reversible binding sites for those agents. Such binding can, for example, be provided by macromolecular materials with polar, hydrogen bonding or, preferably ionic (either anionic or cationic) binding sites. Those materials can be either naturally derived or synthetic, and suitable materials include poly (vinyl pyrrolidone), poly (ethylene glycol), poly (ethylene oxide), poly (acrylic acid), poly (saccharides), and poly (saccharide) derivatives such as aminosachharides chitin and chitosan, glycosaminoglycans (e.g., hyaluronate, chondroitin 4- and 6-sulfate, dermatan sulfate, keratan sulfate, heparan sulfate and heparin), proteoglycans, glycoproteins, and glycoloipids. Specific binding components of the implant include heparin, heparan, angiopoietin, agarose and agarose covalently bound to heparin, iota-, kappa- and lambda-carrageenan and a carrageenan covalently bound to heparin.

As noted above, the implant is fabricated of a material which is initially stiff but absorbs fluids and softens upon insertion into the tissue, and for that purpose it may contain a hydrophilic enhancer. Suitable hydrophilic enhancers include compounds containing free hydroxyl groups, amino groups, carboxylic acid groups, sulfonic acid groups, phosphoric acid groups, amide groups, carbonate groups, guanadyl groups, imido groups, and combinations thereof.

The hydrophilic enhancer can also be a poly hydroxy compound such as glycerol, pentaerythritol, propylene glycol, ethylene glycol, diethylene glycol, butane diol, trimethylol propane, and combinations thereof. Other suitable hydrophilic enhancers include ethylene carbonate, propylene carbonate, and combinations thereof; esters of citric acid, esters of tartaric acid, triethyl citrate, diethyl tartrate, and combinations thereof; a saccharide, a substituted saccharide, sorbitol, mannitol, and combinations thereof; and a sugar, a starch, a carbohydrate, and combinations thereof.

In order to facilitate formation of the implant into a desired shape, the implant can also be fabricated of or contain a material having a low surface energy. Suitable materials for that purpose include fatty acid esters of polyols, ester waxes, fatty acid amides, amide waxes, a lipid, a lipid derivative, oils and waxes, paraffins, mineral oil, and combinations thereof.

The fatty acid esters of polyols can be selected from the group consisting of mono-fatty acid ester of glycerol, di-fatty acid ester of glycerol, tri-fatty acid ester of glycerol, ethylene glycol, diethylene glycol, sorbitol, sorbitan monostearate, glycerol monostearate, glycerol tristearate, and combinations thereof.

The ester waxes can be selected from the group consisting of esters of stearic, palmitic acid, lauric acid, oleic acid, ethyl stearate, pentaerythritol stearate, and combinations thereof; the amide waxes can be selected from the group consisting of erucamide, stearamide, and combinations thereof; and the lipid and the lipid derivative can be selected from the group consisting of a triglyceride, lecithin, phosphatidyl choline, and combinations thereof.

It is important that the implant be non-ablatively introduced into the tissue so as not to destroy the tissue. As discussed more fully hereinafter, this can be done either by mechanically cutting a channel into which the implant is inserted or by having the implant cut its own way into the tissue as it is inserted. By inserting the implant in this manner, the temperature of the tissue can be kept below about 50° C. throughout the process.

If desired, an exogenous angiogenic agent can be included in the implant for release into the tissue along with the agents which are produced by the tissue and absorbed by the implant. In this case, the implant serves as a reservoir for controlled release of the exogenous angiogenic agent as well as the autogenous agents, further enhancing and prolonging the angiogenesis and revascularization in the surrounding tissue.

Exogenous angiogenic agents which can be included in the implant include a vascular endothelial growth factor, acidic and basic fibroblast growth factors, an epidermal growth factor, transforming growth factors alpha and beta, a platelet derived endothelial growth factor, tumor necrosis factor alpha, a hepatocyte growth factor, an insulin type growth factor, a bone growth factor and combinations thereof.

The implant can also contain a bioactive agent selected from the group consisting of nucleic acid constructs capable of synthesizing growth factors, cytokines, angiogenic factors, and combinations thereof. Suitable nucleic acid constructs include replication-deficient adenovirus vectors comprising a transgene coding for an angiogenic protein or peptide selected from the group consisting of vascular endothelial growth factor, fibroblast growth factor, platelet derived growth factor, autologous growth factors, transforming growth factor, and combinations thereof.

Other therapeutic agents which can be included in the implant to enhance the function of hypoxic tissue include agents separated from or found in concentrates of autologous tissue, particularly agents in autologous blood plasma or cardiovascular tissue; agents separated from or found in concentrates of allogenous or allograft tissue, particularly agents in allogenous or allograft cardiovascular tissue; living cells separated from autologous tissue, then grown and repopulated ex vivo, together with nutrients and media, and scaffold structures used to encourage cell growth and define cell population shape, particularly myocardial cells and human vascular endothelial cells; and natural or synthetic anti-adhesion agents, such as those derived from hyaluronic acid, hyaluronan or chemical (esterification) modification thereof, or agents based on poly alkylene oxides such as poly ethylene oxide or poly ethylene glycol.

The implant is of relatively small size, with a preferred diameter on the order of 50 micrometers to 1.0 millimeters, and a length on the order of 5 to 20 millimeters. Rather than using a single larger implant, it is preferable to use a plurality of smaller ones. That has been found to be less damaging to the tissue as well as permitting greater flexibility in the delivery system.

In the treatment of the heart tissue, the implant is preferably introduced into the myocardial tissue quickly and at a time in the cardiac cycle when the heart is fully expanded and the tissue is at rest, and a system for delivering the implant in this manner is illustrated in FIG. 2. This system includes a handheld instrument 26 that includes a delivery head 27 which carries the implant 21 and is driven by an actuator 28. In the embodiment illustrated, the actuator is a double acting pneumatic cylinder, but other suitable actuators can also be utilized, if desired. The pneumatic actuator is particularly suitable since it can be driven both in a forward direction to insert the implant and in a reverse direction to withdraw the delivery head. This can be done quite rapidly, e.g. about 10 to 500 milliseconds or less, which makes it possible to complete the insertion of the implant while the heart is at rest.

Compressed air or other pressurized gas is supplied to the actuator from a source 29 through a pressure regulator 31 and a solenoid operated control valve 32. The source can be a compressor or another suitable source of pressurized gas, such as a cylinder or bottle. Operating power is applied to the control valve from a DC source 33 through a control circuit 34.

An EKG monitor 36 provides a signal corresponding to the patient's heartbeat, and that signal is monitored by control circuit 34. Operation of the system is initiated by a footswitch 37 or other suitable switch connected to the control circuit. Actuation of that switch enables the control circuit which then monitors the EKG signal for a characteristic feature, such as the QRS peak. A predetermined after detecting that feature, the control circuit actuates the control valve for a predetermined period of time to drive the actuator and the delivery head in the forward direction. At the end of that period, the control circuit reverses the signal applied to the control valve, and the actuator is driven in the reverse direction to retract the delivery head. Thus, once the surgeon give the command by actuating the footswitch, the system automatically inserts the implant at the proper point in the cardiac cycle.

FIGS. 3–6 illustrate an implanter which is particularly suitable for use during open heart operative procedures where the chest cavity has been opened and the heart is largely exposed. This instrument can be used to insert implants through the pericardium and into the myocardium.

In this embodiment, the actuator 28 is mounted in a generally cylindrical housing body 38 which is adapted to be held in the hand of a surgeon, with fittings 41, 42 for connection to pneumatic lines (not shown). A removable end cap 43 is secured to the forward end of the housing body by a nut 44 on a threaded boss 45 at one end of the body of the actuator.

The delivery head 27 is mounted on the output shaft 46 of the actuator at the forward end of the housing for movement between retracted and extended positions, as shown in FIGS. 3 and 6, respectively. The delivery head comprises a length of hypodermic tubing 47 which is affixed to a male Leur fitting 48. That fitting is connected to a female Leur fitting 49 which is threadedly mounted on the output shaft.

A portion of tubing 47 is cut away to form a recess 51 in which the implant is carried, and the distal end of the tubing is cut at an angle to form a tip 52 for cutting a channel in the tissue ahead of the implant. In one presently preferred embodiment, the tubing has an outer diameter of about 0.050 inch and an inner diameter or bore 53 of about 0.042 inch, with the implant having a diameter of about 0.025 to 0.040 inch. The recess is formed by cutting away the side wall to a depth of about 0.030 inch and for a length of about 0.197 inch from the cutting tip. The side wall of the tubing is crimped about 0.315 inch from the tip to form a stop 54 for the implant. Prior to deployment, the shaft 21a of the implant is inserted into the bore until the proximal end of the implant abuts the stop, and the distal end rests in the recess near the sharpened tip. Depending upon the size of the implant, the delivery tubing can have a outer diameter on the order of 0.01 inch (0.25 mm) to 0.20 inch (5 mm).

Since the delivery head is removable, the implants and delivery heads can be preassembled together and packaged in sterile packages for installation on the instrument as needed. Following use, the delivery heads can be sterilized for reuse or discarded.

A depth gauge 56 is provided for controlling how far the implant is inserted into the tissue when the delivery head is moved to its extended position. In the embodiment illustrated, the depth gauge has an axially extending shaft 57 which is threadedly mounted in end cap 43, with a U-shaped foot piece 58 at the distal end of the shaft for engagement with the tissue. The effective length of the stroke, i.e. the distance the delivery head extends beyond the foot piece in its extended or advanced position, can be adjusted by screwing the shaft of the depth gauge into and out of the end cap. A lock nut 59 on the shaft can be tightened against the end cap to retain the depth gauge at a desired setting.

As illustrated in FIG. 7, it is also possible to form the implant 21 with a pointed tip 61 and have the implant cut its own way into the tissue as it is inserted. In this embodiment, the distal end 62 of the delivery head tubing 47 is cut square, or blunt, and recess 51 is eliminated. The shaft 21a of the implant is carried within the bore 52 of the tubing, and the pointed tip 61 of the implant extends beyond the distal end of the tubing, with no cutter in front of the implant. This type of implant and delivery head can be utilized in the instrument of FIGS. 3–6 and in other delivery systems, including the other embodiments disclosed hereinafter.

FIG. 8 illustrates an embodiment of the implanter which is particularly suitable for use in endoscopic procedures. It can be used, for example, to insert implants from the pericardium or exterior of the heart into the myocardium.

This embodiment is similar to the embodiment of FIGS. 3–6 in that the actuator 28 is mounted in a generally cylindrical housing body 38 with an end cap 43, which can be held in the hand of the surgeon. In this embodiment, however, the depth gauge comprises a tubular barrel 64 which extends in a forward direction from the end cap, and has a length sufficient to reach through the endoscope. The delivery head 27 is mounted on an extension rod 66 which is attached to the output shaft 46 of the actuator and extends coaxially within the barrel. The depth to which the implant is inserted into the tissue is corresponds to the distance the delivery head extends beyond the distal end of the barrel when the delivery head is in its advanced or extended position. As in the other embodiments, the implant can either cut its own way into the tissue or the delivery head can have a sharpened tip which cuts a channel in the tissue for the implant.

FIG. 9 illustrates an embodiment of the implanter for use in percutaneous transluminal procedures. It can, for example, be inserted through the femoral or brachial arteries, and utilized for inserting implants into the myocardium from the endothelium or interior of the heart.

Here again, the actuator 28 is mounted in a generally cylindrical housing body 38 with an end cap 43, which can be held in the hand of the surgeon. An elongated, catheter-like, flexible delivery tube 67 extends from the end cap, and the delivery head 27 is mounted on a flexible wire 68 which is attached to the output shaft 46 of the actuator for movement between extended and retracted positions within the delivery tube. The length of the delivery tube is typically on the order of about 120 to 180 cm, but can be longer or shorter, as desired. The wire is preferably metal, but can be made of another material, if desired, as long as it is stiff enough to drive the implant into the tissue and flexible enough to follow a tortuous path into the body. As in the other embodiments, the implant can either cut its own way into the tissue or the delivery head can have a sharpened tip which cuts a channel in the tissue for the implant.

The catheter-like delivery tube can either be introduced directly into the arteries or it can be introduced through a another catheter. If desired, the delivery tube can be formed with one or more additional lumens for guide wires, fluid delivery, and the like.

The implant is preferably form ed with a shape which resists migration within the tissue. In the embodiment of FIG. 10, for example, the implant has a body 71 in the shape of an arrow, with a head 72 with barbs 73 toward one end thereof. In the embodiment of FIG. 11, the body 74 is in the form of a double arrow, with barbed heads 76 toward both ends, and the embodiment shown in FIG. 12 has a rectangular body 77 with barbs 78 at the corners. FIGS. 13 and 14 illustrate embodiments which have bodies 81 in the shape of an S-curve, with hooks or barbs 82, and FIG. 15 illustrates an embodiment in which the body 83 is helical.

In applications in which it is desired to monitor the position of the implant by ultrasonic imaging, means can be included for enhancing visibility of the device in such imaging. Enhanced ultrasound contrast can, for example, be provided by including gas-filled volumes or liquid-filled volumes, such as microspheres, within the body of the implant. Such enhancement can also be achieved by including a closed cell foam structure within the body of the implant and/or by the use of surface grooves which reelect ultrasonic energy. The spacing and depth of the grooves can be selected for optimized reflection of a desired frequency or frequencies.

With implants which are biodegradable and/or bioresorbable, it is desirable that any echogenic contrast agent added to the implant likewise be biodegradable and/or bioresorbable. One example of an echogenic agent which is suitable for this purpose a gas encapsulated within an albumin shell. Biodegradable echogenic agents which are suitable for use in such applications are available commercially from Molecular Biosystems and Rush Medical under the tradenames Albunex and Optison.

It is likewise possible to enhance the visibility of the implant to imaging systems such as fluoroscopes which are based upon differential absorption of radiation such as X-rays by various structures within the body. This can be done by including elements, molecules, compounds or compositions in the implant which have atomic weights that are sufficient to confer radiopacity to the implant. Such elements generally have atomic weights greater than 19, with the elements having higher atomic weights being preferred since lesser amounts of them are required to make the implant fully visible. Radiopaque materials which include a substantial proportion of elements having atomic weights greater than 100 are particularly preferred, e.g. barium, gold, platinum, tantalum, bismuth and iodine.

The radiopacifying agents can be incorporated into the implants in several ways. Biocompatible non-immunogenic metals such as gold and platinum may be incorporated as a very fine dispersion with particle sizes less than a few micrometers. Other heavy atoms may be incorporated in the form of inorganic salts, such as barium sulfate. Organic compounds containing chemically bonded iodine are also a preferred form of radiopaque material, particularly those which are water soluble and contain more than 10 percent iodine, by weight. From a pharmacokinetic standpoint, once released from the implant, the radiopaque medium should be readily eliminated from the body, such as by standard renal function.

The invention has a number of important features and advantages. It does not require the use of lasers, and is far less expensive than the laser systems which are currently being employed in other vascularization and revascularization procedures. The non-ablative introduction of the implant avoids damage to the tissue, and studies have shown that greater levels of angiogenesis are stimulated than with a conventional laser treatment. It is also highly portable and easy to use. While the invention is particularly suitable for use in the treatment of ischemic heart disease, it can also be used to enhance the function of hypoxic or ischemic tissue, or to increase the vascularity or blood flow of any other tissue.

It is apparent from the foregoing that a new and improved method of enhancing blood flow has been provided. While only certain presently preferred embodiments have been described in detail, as will be apparent to those familiar with the art, certain changes and modifications can be made without departing from the scope of the invention as defined by the following claims.

What is claimed is:

1. A method of enhancing blood flow in tissue comprising the steps of:
   non-ablatively introducing an implant into the tissue to stimulate production of angiogenic agents by the tissue;
   absorbing the agents produced by the tissue into the implant;
   storing the absorbed agents in the implant; and
   releasing the stored agents back into the tissue when the production of agents by the tissue subsides.

2. The method of claim 1 wherein the implant is fabricated of a bioresorbable material and is resorbed into the tissue after the agents are released.

3. The method of claim 1 wherein the implant is introduced into the tissue in a relatively stiff form, then softens to form a compliant gel that can absorb the agents produced by the tissue.

4. The method of claim 1 wherein the agents which are absorbed and released include VEGF, aFGF, bFGF and PDGF growth factors, and angiopoietin.

5. The method of claim 1 including the steps of including an exogenous angiogenic agent in the implant, and releasing the exogenous agent into the tissue along with the agents which are produced by the tissue and absorbed by the implant.

6. The method of claim 5 wherein the exogenous angiogenic agent is selected from the group consisting of a vascular endothelial growth factor, acidic and basic fibroblast growth factors, an epidermal growth factor, transforming growth factors alpha and beta, a platelet derived endothelial growth factor, tumor necrosis factor alpha, a hepatocyte growth factor, an insulin type growth factor, a bone growth factor and combinations thereof.

7. A method of enhancing the function of hypoxic tissue comprising the steps of:
   non-ablatively introducing an implant into the hypoxic tissue to stimulate production of angiogenic agents by the tissue;
   absorbing the agents produced by the tissue into the implant;
   storing the absorbed agents in the implant; and
   releasing the stored agents back into the hypoxic tissue when the production of agents by the tissue subsides.

8. The method of claim 7 wherein the implant is fabricated of a bioresorbable material and is resorbed into the tissue after the agents are released.

9. The method of claim 7 wherein the implant is introduced into the tissue in a relatively stiff form, then softens to form a hydrodynamic gel that can absorb the agents produced by the tissue.

10. The method of claim 7 wherein the agents which are absorbed and released include VEGF, aFGF, bFGF and PDGF growth factors, and angiopoietin.

11. The method of claim 7 including the steps of including an exogenous angiogenic agent in the implant, and releasing the exogenous agent into the tissue along with the agents which are produced by the tissue and absorbed by the implant.

12. The method of claim 11 wherein the exogenous angiogenic agent is selected from the group consisting of a vascular endothelial growth factor, acidic and basic fibroblast growth factors, an epidermal growth factor, transforming growth factors alpha and beta, a platelet derived endothelial growth factor, tumor necrosis factor alpha, a hepatocyte growth factor, an insulin type growth factor, a bone growth factor and combinations thereof.

13. A method of enhancing the function of ischemic tissue comprising the steps of:
   non-ablatively introducing an implant into the ischemic tissue to stimulate production of angiogenic agents by the tissue;
   absorbing the agents produced by the tissue into the implant;
   storing the absorbed agents in the implant; and
   releasing the stored agents back into the ischemic tissue when the production of agents by the tissue subsides.

14. The method of claim 13 wherein the implant is fabricated of a bioresorbable material and is resorbed into the tissue after the agents are released.

15. The method of claim 13 wherein the implant is introduced into the tissue in a relatively stiff form, then softens to form a hydrodynamic gel that can absorb the agents produced by the tissue.

16. The method of claim 13 wherein the agents which are absorbed and released include VEGF, aFGF, bFGF and PDGF growth factors, and angiopoietin.

17. The method of claim 13 including the steps of including an exogenous angiogenic agent in the implant, and releasing the exogenous agent into the tissue along with the agents which are produced by the tissue and absorbed by the implant.

18. The method of claim 17 wherein the exogenous angiogenic agent is selected from the group consisting of a vascular endothelial growth factor, acidic and basic fibroblast growth factors, an epidermal growth factor, transforming growth factors alpha and beta, a platelet derived endothelial growth factor, tumor necrosis factor alpha, a hepatocyte growth factor, an insulin type growth factor, a bone growth factor and combinations thereof.

19. A method of treating ischemic heart disease comprising the steps of:
   non-ablatively introducing an implant into the myocardial tissue to stimulate production of angiogenic agents by the tissue;
   absorbing the agents produced by the myocardial tissue into the implant;
   storing the absorbed agents in the implant; and
   releasing the stored agents back into the myocardial tissue to promote revascularization of the tissue when the production of agents by the tissue subsides.

20. The method of claim 19 wherein the implant is fabricated of a bioresorbable material and is resorbed into the myocardial tissue after the agents are released.

21. The method of claim 19 wherein the implant softens shortly after introduction into the myocardial tissue and becomes compliant with the contractile motion of the heart.

22. The method of claim 19 wherein the implant is introduced into the myocardial tissue in a relatively stiff form, then softens to form a hydrodynamic gel that can absorb the agents produced by the tissue.

23. The method of claim 19 wherein the agents which are absorbed and released include VEGF, aFGF, bFGF and PDGF growth factors, and angiopoietin.

24. The method of claim 19 including the steps of including an exogenous angiogenic agent in the implant, and releasing the exogenous agent into the myocardial tissue along with the agents which are produced by the tissue and absorbed by the implant.

25. The method of claim 24 wherein the exogenous angiogenic agent is selected from the group consisting of a vascular endothelial growth factor, acidic and basic fibroblast growth factors, transforming growth factors alpha and beta, a platelet derived endothelial growth factor, an insulin type growth factor, and combinations thereof.

26. The method of claim 19 wherein the implant is introduced into the myocardial tissue at a time in the cardiac cycle when the heart is fully expanded and the tissue is at rest.

* * * * *